(12) United States Patent
Kim

(10) Patent No.: US 9,982,354 B2
(45) Date of Patent: May 29, 2018

(54) ASEPTIC AND ODORLESS NITRIC OXIDE GENERATOR

(71) Applicant: EUNHAE ENC CO., LTD, Gyeonggi-do (KR)

(72) Inventor: Bu Yeol Kim, Gyeonggi-do (KR)

(73) Assignee: EUNHAE ENC CO., LTD, Siheung-si, Gyeonggi-do (KR)

( * ) Notice: Subject to any disclaimer, the term of this patent is extended or adjusted under 35 U.S.C. 154(b) by 548 days.

(21) Appl. No.: 14/647,828

(22) PCT Filed: Dec. 11, 2013

(86) PCT No.: PCT/KR2013/011473
§ 371 (c)(1),
(2) Date: Sep. 10, 2015

(87) PCT Pub. No.: WO2014/092453
PCT Pub. Date: Jun. 19, 2014

(65) Prior Publication Data
US 2016/0010231 A1    Jan. 14, 2016

(30) Foreign Application Priority Data

Dec. 13, 2012 (KR) .......................... 10-2012-0145108

(51) Int. Cl.
*B01J 19/08* (2006.01)
*A61L 9/22* (2006.01)
(Continued)

(52) U.S. Cl.
CPC ............... *C25B 15/02* (2013.01); *A61L 9/22* (2013.01); *B01D 53/30* (2013.01); *B01D 53/323* (2013.01);
(Continued)

(58) Field of Classification Search
CPC ......... A61L 9/22; C01B 21/203; B01J 19/088
See application file for complete search history.

(56) References Cited

U.S. PATENT DOCUMENTS 5,396,882 A * 3/1995 Zapol .................... A61M 15/02
128/200.14
6,955,790 B2 * 10/2005 Castor ....................... B01J 8/02
422/186.04
(Continued)

FOREIGN PATENT DOCUMENTS

KR    10-0477060 B1    3/2005
KR    10-0564660 B1    3/2006
(Continued)

*Primary Examiner* — Nicholas A Smith
(74) *Attorney, Agent, or Firm* — Luoh J. Wu; Continent Patent Office LLP

(57) ABSTRACT

An aseptic and odorless nitric oxide generator according to the present invention removes harmful materials such as ozone ($O_3$), nitrogen dioxide ($NO_2$) and the like, which are generated during discharge from a high-voltage discharge unit, by contacting the same with respective catalysts at a catalytic reaction unit, reduces noise, which is generated in a discharging process, by using a sound-absorbing material provided inside an exhaust pipe, and receives measured data from respective sensors provided inside the exhaust pipe so as to allow a control unit to execute and automatically operate a feedback control, thereby supplying and circulating indoors the air containing aseptic and odorless high-quality nitric oxide, and thus is very appropriate for the nitric oxide absorption by a person residing indoors through the mouth, the skin and a breathing process.

7 Claims, 3 Drawing Sheets

(51) Int. Cl.
  *C01B 21/20* (2006.01)
  *C25B 15/02* (2006.01)
  *B01D 53/30* (2006.01)
  *B01D 53/32* (2006.01)
  *C25B 9/06* (2006.01)

(52) U.S. Cl.
  CPC ........... *B01J 19/088* (2013.01); *C01B 21/203* (2013.01); *C25B 9/06* (2013.01); *B01D 2257/90* (2013.01); *B01D 2257/91* (2013.01); *B01D 2258/06* (2013.01)

(56) References Cited

U.S. PATENT DOCUMENTS

2012/0207647 A1\* 8/2012 Kim .................. A61L 9/22
 422/107
2014/0251787 A1\* 9/2014 Montgomery .......... C01B 21/32
 204/179

FOREIGN PATENT DOCUMENTS

| KR | 10-0957771 B1 | 5/2010 |
| KR | 10-1005516 B1 | 1/2011 |

\* cited by examiner

[Fig. 1]
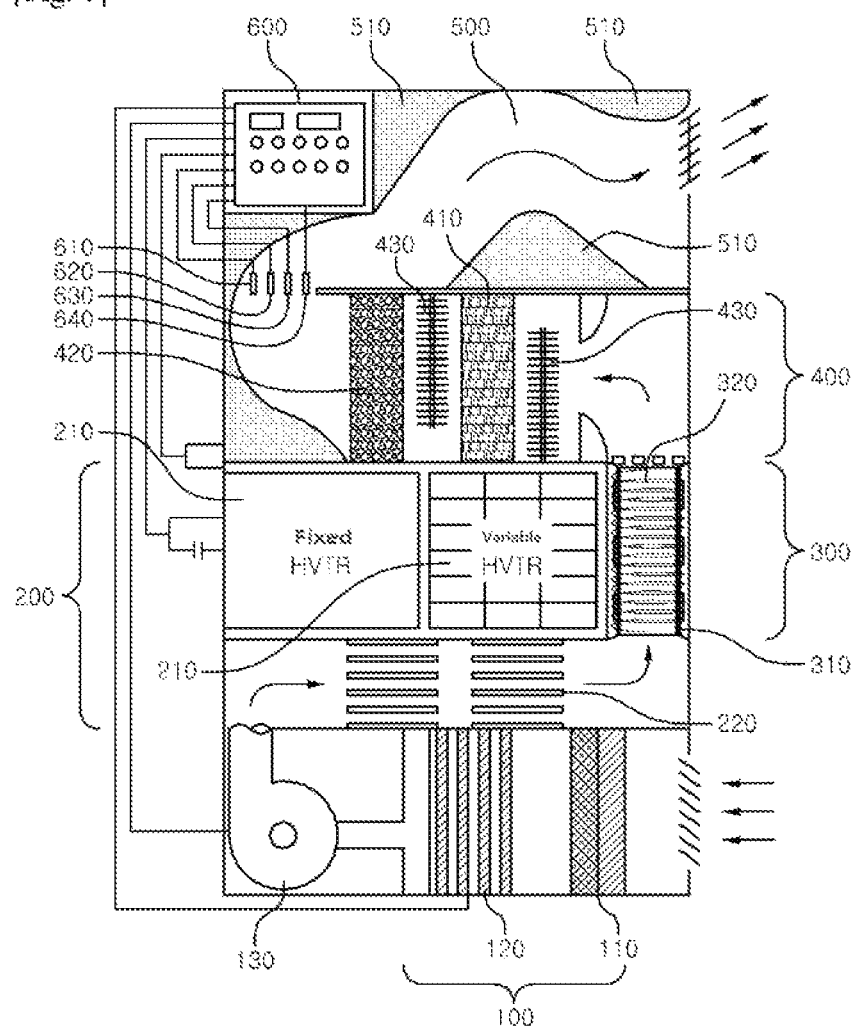
[Fig. 2]
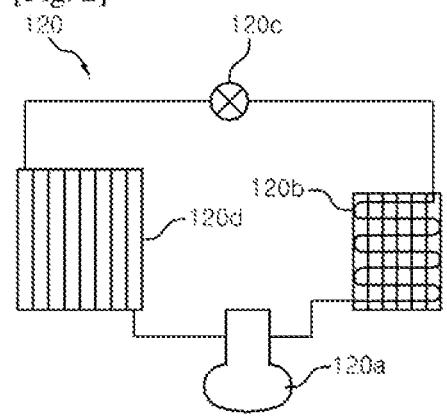

[Fig. 3]
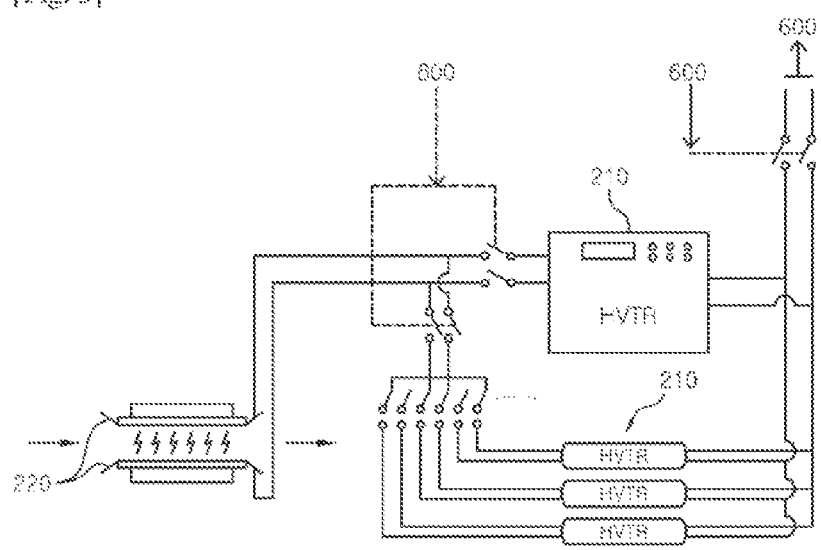
[Fig. 4]
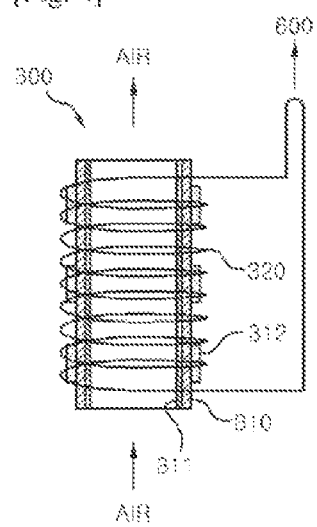
[Fig. 5]
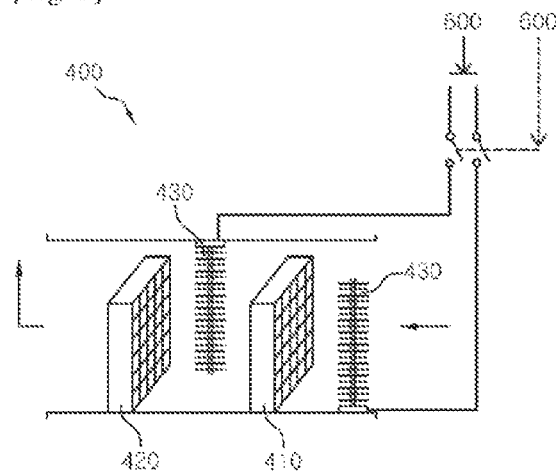

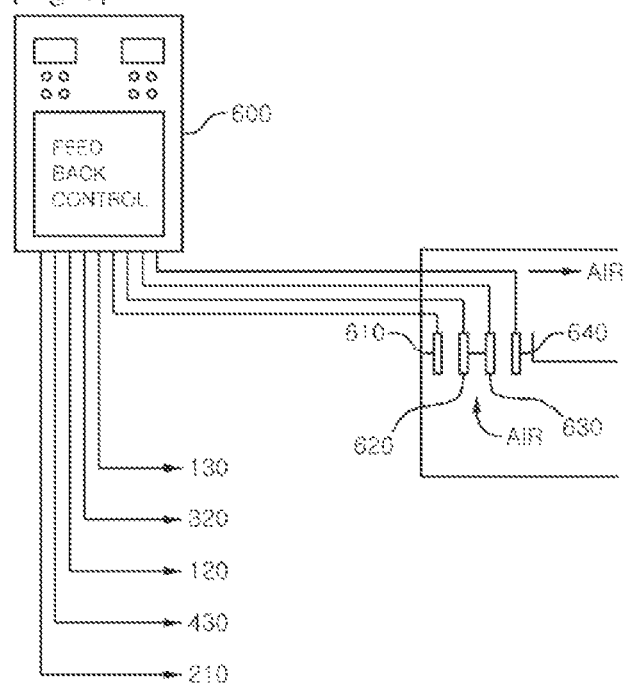

ASEPTIC AND ODORLESS NITRIC OXIDE GENERATOR

TECHNICAL FIELD

The present invention relates to an aseptic and odorless nitrogen oxide generator, and more specifically to an aseptic and odorless nitrogen oxide generator which applies a very high field electron energy generated by a high-voltage discharge unit to the contaminated indoor air in order to breakdown the covalent bond between nitrogen ($N_2$) molecules and oxygen ($O_2$) molecules in the air by an electrochemical reaction, thereby generating nitric oxide (NO), and simultaneously removes malodorous materials and contaminated materials, and performs sterilization by active molecules having strong sterilizing power.

BACKGROUND OF THE INVENTION

There have been many changes in the human living environment and living means due to economic development following industrialization, and increased indoor dwelling time due to development of information communication technology has led to a new environmental problem of indoor air contamination.

When contaminated air is generated in limited space such as the indoors, concentration of the contaminated air increases over time due to circulation of the contaminated materials, thereby an individual may be exposed to microbiological harmful factors such as infectious bacteria and mold including various dust, and this may result in body fatigue, malaise, headache, and infectious diseases and hypersensitivity diseases in the respiratory system and the integumentary system.

In addition, such contamination of indoor air can increase risk of infection for patients in immunocompromised state and elderly patients. Further, research results have shown that intake of various harmful materials due to contamination of indoor air quality, work-related stress and blood flow disorders cause negative effect by increasing the numerical value of reactive oxygen species (ROS) within the body of patients and indoor residents.

The increase in reactive oxygen species as stated above is generated through various metabolic processes when oxygen absorbed into the body during respiration is used in oxidation processes of the body. The oxygen attacks biological tissues to destroy lipids, proteins, and nucleic acids (DNA, RNA), inhibits enzyme function, and promotes a variety of diseases (cancer, aging, etc.), but this also affects neurotransmitters DOPAMINE SEROTOMIN and ACETYL-CHOLINE, as well as ACETYL-CHOLINE ESTERASE, thereby significantly decreasing the immune function.

Meanwhile, research has actually been underway since 1980 based on research results in which nitric oxide (NO) was found to promote health of the cardiovascular system through vasodilation and the antioxidative activity (SOD) which reduces levels of reactive oxygen species in the body.

In particular, the study on nitric oxide as above is derived from the discovery of endothelium-derived relaxing factor (EDRF), and there have been reports of unknown strong blood vessel relaxing factor being produced in the endothelial cells of the blood vessels (EDRF), with the EDRF being identified as nitric oxide (NO).

Nitric oxide (NO) is produced together with L-citrulline by nitrogen monoxide (NO) generating element (NITRIC-OXIDE SYNTHASE; NOS) in L-arginine, and research results have been reported where in regards to the nitric oxide activity in the body, nitric oxide was produced in the vascular endothelial cells to activate guanylate cyclase of the vascular smooth muscle and cyclic GMP were produced to relax the blood vessels. As this study progressed, various other functions of nitric acid (NO) were discovered one after the other in addition to nitric acid (NO) being a signaling molecule playing a key role in the cardiovascular system.

In addition, nitric oxide (NO) is currently known to perform various functions such as blood flow regulator of various body organs, blood pressure regulator, and neurotransmitter in the nervous system fighting infections. Further, the in-depth study by Robert F. Furchgott, phD, Louis Ignarro, phD and Ferid Murad, phD on how the nitric oxide (NO) exists in almost all organisms and is produced by a variety of different types of cells was recognized for its achievement in 1998, thereby the above three researchers were awarded the Nobel Prize in Physiology or Medicine by the Nobel Committee at the Karolinska Institutet in recognition of their merit on "discovering nitrogen monoxide (NO: NITRIC OXIDE) as the signaling molecule in the cardiovascular system".

However, the endothelial cells by itself cannot produce enough nitric acid required for physiological functions in the body due to various factors such as contamination of indoor air quality, nutritional deficiencies in the diet, lack of exercise, overwork and drug intake. Thus, the nitric acid must be directly or indirectly supplied from outside through various means.

As an example, there exist a method of producing nitric acid for producing nitric oxide (NO), that is, nitrogen monoxide is produced in the process of oxidizing ammonia with oxygen and carrying out absorption in water. However, this method could not be practically used due to the ammonia material being harmful to the body, increased malodor concentration and having fire risk.

In response to the above, the Korean Patent No. 10-0203721 (Method and Apparatus for Production of Nitric Oxide Gas Mixture) introduced a method of placing feed gas containing oxygen and nitrogen, oxygen and ammonia, and oxygen and ammonia nitrogen to a Group VIII catalyst within a temperature range of about 300~1200 degrees Celsius in order to produce a mixture containing nitrogen dioxide. However, this method requires a separate heating apparatus for raising the gas temperature to 300~1200 degrees Celsius resulting in excessive energy cost, and the ammonia gas used in the process affects the respiratory system. Also, inherent fire risk exists which requires separate safety measures.

In addition, the Korean Patent No. 10-0978805 (Refining Method and Equipment of High Purity Nitric Oxide using Cryogenic Freezing Trap) introduced a method in which low-temperature cooling was performed on nitrogen monoxide gas flowing in from the low purity nitrogen monoxide feed tank, which was then passed through an absorbent to remove impurities, and afterwards underwent phase change at low temperature to carry out secondary removal of impurities, and refined nitrogen monoxide at very high vacuum. However, this method requires a separate low purity nitrogen monoxide feed apparatus, the apparatus is complex due to components such as cryogenic freezing system and reaction tank, and has high energy consumption.

Thus, nitric oxide generator developed until now have selectively used ammonia which is a toxic and combustible material harmful to the body, required a separate heating apparatus for raising the gas temperature to a range of 300~1200 degrees Celsius, had increased operating and maintenance costs due to high energy consumption, had high initial investment costs since separate nitric oxide feed apparatus and cryogenic freezing system were required, and the large size of the apparatus limited the apparatus from being purchased for use at homes or business facilities.

SUMMARY OF THE INVENTION

Technical Problem

Accordingly, the present invention has been configured to solve the above problems, and an objective of the present invention is to provide an apparatus easily producing nitric oxide using high field electron energy generated by a high-voltage discharge, but also degrading and removing malodorous materials and contaminated materials existing in the air, and producing aseptic and odorless nitric oxide through sterilizing effect of the active molecules.

Technical Solution

The present invention which aims to achieve the above objective provides an aseptic and odorless nitric oxide generator comprising, an intake pipe established on one side of the housing as a passage for inflow of contaminated air, provided with a pretreatment filter for removing dust from the contaminated air at the inlet in the inner portion thereof, a cooling part installed at a distance away from the pretreatment filter for forced cooling of introduced contaminated air, and an air fan for forced inflow of contaminated air;

A high-voltage discharge unit provided with a high-voltage generator which generates field electron energy to cause an electrochemical reaction in the contaminated air that is suctioned in by the air fan, and discharge electrodes receiving the high-voltage generator and discharging field electron energy;

A magnetic field processor provided with an induction coil for maintaining an excited state by applying a magnetic field to the contaminated air transferred through the high-voltage discharge unit, a magnetic layer established on an inner peripheral surface and a permanent magnet established on an outer peripheral surface of a supporting pipe receiving the induction coil;

A catalytic reaction unit consisting of a first catalyst layer removing ozone and a second catalyst layer removing nitrogen dioxide created during high voltage discharge, the catalyst layers being connected to the magnetic field processor, and an electric heater provided between each catalyst layer for activating the catalytic reaction;

An exhaust pipe connected to the catalytic reaction unit for discharging nitric oxide produced through the electrochemical reaction to the outside, having a sound-absorbing material attached to the inner peripheral surface thereof to reduce sound generated at the high-voltage discharge process;

Sensors installed in the exhaust pipe for measuring concentrations of nitrogen dioxide, ozone and nitric oxide; and a controller receiving measurement data from the sensors to control input/output voltage regulation of the high-voltage generator of the high-voltage discharge unit, power supply controller of the electric heater of the catalytic reaction unit, the cooling system and the magnetic field processor.

Advantageous Effects

As described above, the aseptic and odorless nitric oxide generator of the present invention can apply a very high field electron energy created through high-voltage discharge to contaminated indoor air in order to produce nitric oxide (NO) by breaking down the covalent bonds of the nitrogen ($N_2$) and oxygen ($O_2$) molecules in the air via the electrochemical reaction, and it is possible to degrade and remove malodorous materials and contaminated materials in the air simultaneously with strong sterilization by the active molecules. Not only that, electrochemical reaction can be continued via extension of the contact time with the active molecules by applying a magnetic field to the excited air, thereby increasing nitric oxide (NO) production, and the sterilization efficiency and the removal efficiency of contaminated materials and malodorous materials can be significantly improved.

In addition, harmful materials such as ozone ($O_3$) and nitrogen dioxide ($NO_2$) produced during discharge at the high-voltage discharge unit is removed by contact with each catalyst in the catalytic reaction unit, and the noise generated during the discharge process is reduced by the sound-absorbing material installed inside the exhaust pipe. Further, measurement data is received from each sensor installed inside the exhaust pipe to perform automatic driving and FEEDBACK control at the controller, resulting in air containing aseptic and odorless high quality nitric oxide to be supplied to and circulated indoors, such that it is very suitable for nitric oxide to be absorbed through the mouth, skin, and breathing process of a person residing indoors.

BRIEF DESCRIPTION OF THE DRAWINGS

FIG. 1 is an overall system diagram of the nitric oxide generator according to the present invention.

FIG. 2 is a block diagram showing a cooling part of the nitric oxide generator of FIG. 1.

FIG. 3 is a block diagram showing a high-voltage discharge unit of the nitric oxide generator of FIG. 1.

FIG. 4 is a block diagram showing a magnetic field processor of the nitric oxide generator of FIG. 1.

FIG. 5 is a block diagram showing a catalytic reaction unit of the nitric oxide generator of FIG. 1.

FIG. 6 is a block diagram showing a controller of the nitric oxide generator of FIG. 1.

DESCRIPTION OF THE PREFERRED EMBODIMENTS

Hereinafter, the nitric oxide generator of the present invention will be described with reference to the accompanying drawings, but the present invention is not limited to the illustrated embodiments.

FIG. 1 is an overall system diagram of the nitric oxide generator according to the present invention. Referring to the figure, the nitric oxide generator of the present invention comprises an intake pipe (100) largely established on one side of the housing, a high-voltage discharge unit (200) for causing an electrochemical reaction of the contaminated air, a magnetic field processor (300) for maintaining an excited state of the contaminated air, a catalytic reaction unit (400) for removing ozone and nitrogen dioxide, an exhaust pipe (500) for discharging nitric oxide produced through the electrochemical reaction to the outside, and a controller (600) receiving measurement data from sensors to control voltage regulation and power supply, etc.

First, the nitric oxide generator of the present invention comprises a housing (not shown) of a fixed volume to accommodate the main components described above, having an intake pipe (100) on one side thereof for suctioning indoor air inside, such intake pipe (100) being provided with a pretreatment filter (110) in the inner portion of the inlet for removing dust from the contaminated air, a cooling part (120) installed at a distance away from the pretreatment filter (110) for forced cooling of introduced contaminated air, and an air fan (130) for forced inflow of contaminated air.

The indoor air flowing into the intake pipe (100) has fine dust removed by the pretreatment filter (110) installed at the inlet of the intake pipe (100), and then it is transferred to a cooling part (120) which is installed adjacent to the pretreatment filter (110).

FIG. 2 is a block diagram showing a cooling part of the nitric oxide generator of FIG. 1. As illustrated, in the cooling part (120), a cooling liquid is compressed with high temperature and high pressure at the compressor (120a), then transferred to a condenser (120b) to be condensed by air-cooling or water-cooling, expanded to a fluid having low temperature and low pressure at the expansion valve (120c), then cooled to the predetermined temperature through heat-exchange at the cooling coil (120d) by the evaporation heat that is generated when the cooling fluid is evaporated through indirect contact with the contaminated air flowing into the cooling coil (120d).

Through this, pressure required for discharging the indoor air, which was forcibly suctioned in by the air fan (130), back outside after passing through the high-voltage discharge unit, magnetic field processor and the catalytic reaction unit is provided.

The contaminated air passed through the intake pipe (100) as above is transferred to the high-voltage discharge unit (200), and at a high-voltage generator (210), removes various malodorous materials, performs sterilization treatment and produces nitric oxide through electrochemical reaction process according to high-voltage discharge.

FIG. 3 is a cross-sectional view showing a high-voltage discharge unit of the nitric oxide generator of FIG. 1. As illustrated, field electron energy generated at a high-voltage generator (210) is discharged after being supplied to discharge electrodes (220), and nitric oxide (NO) is produced by breaking down covalent bonds of nitrogen ($N_2$) and oxygen ($O_2$) molecules of the contaminated indoor air flowing in between the discharge electrodes via electrochemical reaction such as dissociation, ionization, excitation, oxidation and reduction. Further, the covalent bond of contaminated materials and malodorous material molecules are broken down and removed, and the bacteria in the air is sterilized by active molecules such as OH-Radical and reactive oxygen species produced during the electrochemical reaction.

The discharge electrodes (220) are a combination of discharge electrode (+electrode) and ground electrode (−electrode) or a combination of discharge electrode, dielectric and ground electrode. Here, the material for the discharge electrode and the ground electrode is selected from among stainless steel containing tungsten, titanium, nickel and chromium component, or hastelloy containing nickel, chromium, germanium and zirconium component, or molybdenum disilicide, and the inner surface is coated with a catalyst selected from among titanium dioxide ($TiO_2$), zircon ($ZrSiO_4$), and lithium hydroxide (LiOH) in order to improve the discharge efficiency.

Here, the field electron energy(IE,eV) at the output side of the high-voltage discharge unit (210) is higher than field electron energy(IE,eV) 12.0857 eV which can degrade the covalent bonds of oxygen ($O_2$) molecules in the air; higher than field electron energy(IE,eV) 15.581 eV which can degrade the covalent bonds of nitrogen ($N_2$) molecules; higher than field electron energy(IE,eV) 10.86 eV which can degrade the covalent bonds of formaldehyde (HCHO) that is a representative material of sick building syndrome; higher than field electron energy(IE,eV) 8.828 eV which can degrade the covalent bonds of toluene ($C_7H_8$) that is one of volatile organic compounds (VOCs); higher than field electron energy(IE,eV) 13.777 eV which can degrade the covalent bonds of carbon dioxide ($CO_2$) that is an indoor ventilation index material; higher than field electron energy(IE, eV) 14.0414 eV which can degrade the covalent bonds of carbon monoxide (CO) that is a product of incomplete combustion causing blood coagulation and headaches; higher than field electron energy(IE,eV) 10.07 eV which can degrade the covalent bonds of ammonia ($NH_3$) that is a malodorous material; higher than field electron energy(IE, eV) 10.457 eV which can degrade the covalent bonds of hydrogen sulfide ($H_2S$); higher than field electron energy (IE,eV) 2.88 eV which can degrade the C—N bonds among the atomic bonds of malodorous materials and contaminated materials; higher than field electron energy(IE,eV) 4.03 eV which can degrade the N—H bonds; higher than field electron energy(IE,eV) 4.30 eV which can degrade the C—H bonds; higher than field electron energy(IE,eV) 3.41 eV which can degrade the C—C bonds; and higher than field electron energy(IE,eV) 7.08 eV which can degrade the C=O bonds.

Therefore, it is preferable for the high-voltage generator (210) of the present invention to use voltage consisting of direct current (DC) of 12V or more and alternating current (AC) of 110V or more at the input side, and voltage at a range of 1 KV or more to 300 KV and frequency (Hz) at a range of 1 KHz to 100 KHz at the output side.

The high-voltage generator (210) installed in the high-voltage discharge unit (200) for the above purpose can be a plurality of stationary high-voltage generators with an output voltage selected from 1 KV~300 KV, a variable high-voltage generator capable of freely adjusting the output voltage and frequency, or the stationary and variable high-voltage generators can be installed together and used as shown in FIG. 1.

Thus, the electrochemical reaction via the high-voltage generator (210) for the indoor contaminated air which flows in by discharging high field electron energy received is carried out as follows with e representing field electron energy and NM representing Na, K, Ca, and Mg.

First, the dissociation reaction is carried out according to the following steps.
1) $e+O_2 \rightarrow O+O+e$
2) $e+N_2 \rightarrow N+N+e$
3) $e+O_2 \rightarrow O.+O$ Also, the ionization reaction is carried out according to the following steps.
1) $e+N_2 \rightarrow N+N^+ +2e$
2) $e+N_2 \rightarrow N_2^+ +2e$
3) $e+O_2 \rightarrow O+O^+ +2e$
4) $e+O_2 \rightarrow O_2^+ +2e$ [54]

Also, the oxidation reaction is carried out according to the following steps.
1) $e+O_2 \rightarrow O+O$
2) $O+NO+M \rightarrow NO_2+M$
3) $O+H_2O \rightarrow OH+OH$
4) $OH+NO_2 — HNO_3$ Also, the reduction reaction is carried out according to the following steps.
1) $e+N_2 \rightarrow e+N+N$
2) $N+NO \rightarrow N_2+O$ The OH Radical active species production reaction which sterilizes bacteria in the air during the electrochemical reaction process consists of the following steps where production occurs by dissociation of vapor in the air.

1) $e + H_2O \rightarrow H^+ + OH^-$
2) $e + H_2O \rightarrow H + OH + e$
3) $O + H_2O \rightarrow 2OH$ However, the active molecule generated by high-voltage discharge as above has very random activity, thus the contact time between the active molecules and the contaminated and malodorous materials are short, thereby lowering the contact efficiency. Further, since active molecules have a short lifespan, the excited state is not sufficiently maintained enough to properly degrade the contaminated materials and the malodorous materials, thereby there exists a low degradation rate of the contaminated materials and malodorous materials, and it is difficult to expect a significant sterilization effect.

However, the lifespan of the active molecule is significantly extended when a magnetic field is applied to the active molecules produced by high-voltage discharge, and as a result excited state of the contaminated gas containing active molecules can be maintained correspondingly longer.

Therefore, a magnetic field processor (300) is needed for improving contact efficiency by increasing contact time between contaminated materials and malodorous materials in regards to the active molecules contained in the contaminated gas, by extending and inducing in a specific direction the excited state of the contaminated gas that is excited through discharge at the high-voltage discharge unit (200) based on the above properties.

FIG. 4 is a cross-sectional view showing a magnetic field processor of the nitric oxide generator of FIG. 1. As illustrated, the magnetic field processor (300) consists of a supporting pipe (310) of a metal material through which magnetic field passes through, and an induction coil (320) placed at a distance away from the outer peripheral surface of supporting pipe (310) by wrapping around thereto to apply magnetic field to the contaminated air at excited state and to proceed in a particular direction by the electric dipole moment. Further, the inner peripheral surface of the supporting pipe (310) is coated with magnetic powder to form a magnetic layer (311), and the outer peripheral surface of the supporting pipe (310) has a permanent magnet (312) mounted thereon.

Here, the permanent magnet (312) mounted on the outer peripheral surface of the supporting pipe (310) is a neodymium magnet having 3200 gauss or higher, and it is preferable to use an induction coil (320) of solenoid type forming a magnetic field of 1 Tesla or higher.

The induction coil (320) of the magnetic field processor (300) as above aids the excited state to be continued by extending the lifespan of the active molecules by applying a solenoid magnetic field to the contaminated air excited via discharge at the high-voltage discharge unit (200), and at the same time extends the contact time between the active molecules and the contaminated and malodorous materials included in the contaminated gas by aligning the contaminated gas at the excited state and proceeding in a particular direction through the dipole moment.

In addition, the magnetic layer (311) formed on the inner peripheral surface and the permanent magnet (312) mounted on the outer peripheral surface of the supporting pipe (310) also apply magnetic field in the same manner to increase nitric oxide (NO) generation rate through continued excited state of the contaminated air and increased lifespan of the active molecules, and also further improve removal of malodorous materials and contaminated materials through degradation and sterilization.

The indoor air that has passed through the magnetic field processor (300) in this way is transferred to a catalytic reaction unit (400) to remove harmful materials such as ozone ($O_3$) and nitrogen dioxide ($NO_2$) generated during electrochemical reaction of the contaminated air.

FIG. 5 is a cross-sectional view showing a catalytic reaction unit of the nitric oxide generator of FIG. 1. As illustrated, the catalytic reaction unit (400) consists of a first catalyst layer (410) in which at least one catalytic material selected from among copper oxide (CuO), manganese dioxide ($MnO_2$) and carbon having ozone ($O_3$) degradation characteristic is deposited in a porous carrier or filter media, a second catalyst layer (420) in which at least one catalytic material selected from among zeolite, cerium oxide (CeO), and lithium chloride (LiCl) having nitrogen dioxide ($NO_2$) degradation characteristic is deposited in a porous carrier or filter media, and an electric heater (430) provided between the first catalyst layer (410) and the second catalyst layer (420) or at the side of each catalyst layer (410, 420) for activating the catalytic reaction.

Using the catalytic reaction unit (400) as above, the ozone ($O_3$) generated during the electrochemical reaction process of the contaminated air is removed by the first catalyst layer (410) and the nitrogen dioxide ($NO_2$) generated is removed by the second catalyst layer (420) so that only pure nitric acid is discharged outside through the exhaust pipe (500) which reduces noise generated at the high-voltage discharge process through a sound-absorbing material (510) attached thereon.

FIG. 6 is a block diagram showing a controller of the nitric oxide generator of FIG. 1. As illustrated, a controller (600) carries out real-time operation through a nitric oxide concentration measurement sensor (610), an ozone concentration measurement sensor (620), a nitrogen dioxide concentration measurement sensor (630) and temperature sensor (640) installed on the exhaust pipe (500). If a concentration exceeding a predetermined value input to each sensor is measured, a signal is transmitted to the controller (600) to carry out the FEEDBACK control system input as a program in advance, thereby harmful materials such as ozone and nitrogen dioxide discharged during over-discharge from overproduction is additionally removed by reducing the output voltage by lowering the input voltage supplied to the high-voltage generator (210), or reducing the discharge quantity at the discharge electrodes (220) by cutting off the power supplied to a portion of the multi-installed high-voltage generator, or activating the catalytic reaction and heating of the catalyst layer by supplying power to the electric heater (430) placed on the first and second catalyst layers.

As described above, the nitric oxide generator of the present invention applies a very high field electron energy created through high-voltage discharge to contaminated indoor air in order to produce nitric oxide (NO) by breaking down the covalent bonds of the nitrogen ($N_2$) and oxygen ($O_2$) molecules in the air via the electrochemical reaction such as dissociation, ionization, excitation, oxidation and reduction. Also it is possible to degrade and remove malodorous materials and contaminated materials in the air simultaneously with strong sterilization by the active molecules such as OH-Radical and reactive oxygen species. Not only that, electrochemical reaction is continued through extension of the contact time with the active molecules generated during the high-voltage discharge process while maintaining excited state by applying a magnetic field to the excited air, thereby nitric oxide (NO) production is increased, and the sterilization efficiency and removal efficiency of contaminated materials and malodorous materials is significantly improved.

In addition, harmful materials such as ozone ($O_3$) and nitrogen dioxide ($NO_2$) produced during discharge at the high-voltage discharge unit is removed by contact with each catalyst in the catalytic reaction unit, and the noise generated during the discharge process is reduced by the sound-absorbing material installed inside the exhaust pipe. Further, measurement data is received from each sensor installed inside the exhaust pipe to perform automatic driving and FEEDBACK control at the controller, resulting in air containing aseptic and odorless high quality nitric oxide (NO) to be supplied to and circulated indoors, such that it is very suitable for nitric oxide to be absorbed through the mouth, skin, and breathing process of a person residing indoors.

The invention claimed is:

1. An aseptic and odorless nitric oxide generator comprising,
   an intake pipe established on one side of the housing as a passage for inflow of contaminated air, provided with a pretreatment filter for removing dust from contaminated air at an inlet in an inner portion thereof, a cooling part installed at a distance away from the pretreatment filter for forced cooling of introduced contaminated air, and an air fan for forced inflow of the contaminated air;
   a high-voltage discharge unit provided with a high-voltage generator which generates field electron energy for causing an electrochemical reaction in the contaminated air that is suctioned in by the air fan, and discharge electrodes receiving the high-voltage generator and discharging field electron energy;
   a magnetic field processor provided with an induction coil for maintaining an excited state by applying a magnetic field to the contaminated air transferred through the high-voltage discharge unit, and a supporting pipe receiving the induction coil with a magnetic layer established on its inner peripheral surface and a permanent magnet established on its outer peripheral surface;
   a catalytic reaction unit provided with a first catalyst layer removing ozone and a second catalyst layer removing nitrogen dioxide created during high voltage discharge, and an electric heater provided between each catalyst layer for activating catalytic reaction;
   an exhaust pipe connected to the catalytic reaction unit for discharging, to outside, nitric oxide produced through the electrochemical reaction, having a sound-absorbing material attached to the inner peripheral surface thereof to reduce sound generated at the high-voltage discharge process;
   Sensors installed in the exhaust pipe for measuring concentrations of nitrogen dioxide, ozone and nitric oxide; and
   a controller receiving measurement data from the sensors to control input/output voltage regulation of the high-voltage generator of the high-voltage discharge unit, power supply controller of the electric heater of the catalytic reaction unit, a cooling system and the magnetic field processor.

2. The aseptic and odorless nitric oxide generator as claimed in claim 1, characterized in that the cooling part comprises a compressor for compressing a cooling liquid with high temperature and high pressure, a condenser air-cooling or water-cooling the compressed cooling liquid, an expansion valve expanding the cooling liquid to a fluid having low temperature and low pressure, and a cooling coil carrying out indirect contact of the expanded fluid with the inflow of contaminated air.

3. The aseptic and odorless nitric oxide generator as claimed in claim 1, characterized in that the high-voltage generator has direct current (DC) of 12V or more and alternating current (AC) of 110V or more at the input side, and voltage at a range of 1 KV or more to 300 KV and frequency (Hz) at a range of 1 KHz to 100 KHz at the output side.

4. The aseptic and odorless nitric oxide generator as claimed in claim 3, characterized in that the discharge electrodes are a combination of discharge electrode (+electrode) and ground electrode (−electrode) or a combination of discharge electrode, dielectric and ground electrode, wherein the material for the discharge electrode and the ground electrode is selected from among stainless steel containing tungsten, titanium, nickel and chromium component, or hastelloy containing nickel, chromium, germanium and zirconium component, or molybdenum disilicide, and the inner surface of the discharge electrode is coated with a catalyst selected from among titanium dioxide ($TiO_2$), zirconia ($ZrSiO_4$), and lithium hydroxide (LiOH) to improve discharge efficiency.

5. The aseptic and odorless nitric oxide generator as claimed in claim 4, characterized in that a permanent magnet on an outer peripheral surface of the supporting pipe is a neodymium magnet having 3200 gauss or higher, and the induction coil is a solenoid type forming a magnetic field of 1 Tesla or higher.

6. The aseptic and odorless nitric oxide generator as claimed in claim 5, characterized in that the first catalyst layer of the catalytic reaction unit has at least one catalytic material selected from among copper oxide (CuO), manganese dioxide ($MnO_2$) and carbon with ozone ($O_3$) degradation characteristic deposited in a porous carrier or filter media, and the second catalyst layer of the catalytic reaction unit has at least one catalytic material selected from among zeolite, cerium oxide (CeO), and lithium chloride (LiCl) with nitrogen dioxide ($NO_2$) degradation characteristic being deposited in a porous carrier or filter media.

7. The aseptic and odorless nitric oxide generator as claimed in claim 2, characterized in that the high-voltage generator has direct current (DC) of 12V or more and alternating current (AC) of 110V or more at the input side, and voltage at a range of 1 KV or more to 300 KV and frequency (Hz) at a range of 1 KHz to 100 KHz at the output side.

* * * * *